United States Patent
Pathangay et al.

(10) Patent No.: US 10,185,810 B2
(45) Date of Patent: Jan. 22, 2019

(54) MONITORING DEVICE AND A METHOD OF MONITORING DRUG ADHERENCE IN A CLINICAL TRIAL

(71) Applicant: Wipro Limited, Bangalore (IN)

(72) Inventors: Vinod Pathangay, Bangalore (IN); Santhosh Kumar Madathil, Bangalore (IN)

(73) Assignee: Wipro Limited, Bangalore (IN)

( * ) Notice: Subject to any disclaimer, the term of this patent is extended or adjusted under 35 U.S.C. 154(b) by 249 days.

(21) Appl. No.: 14/981,315

(22) Filed: Dec. 28, 2015

(65) Prior Publication Data

US 2017/0140128 A1 May 18, 2017

(30) Foreign Application Priority Data

Nov. 13, 2015 (IN) .......................... 6118/CHE/2015

(51) Int. Cl.
| | | |
|---|---|---|
| *G01N 33/48* | (2006.01) | |
| *G06F 19/00* | (2018.01) | |
| *A61B 5/0205* | (2006.01) | |
| *G06F 1/32* | (2006.01) | |
| *G16H 10/20* | (2018.01) | |
| *G06G 7/58* | (2006.01) | |

(52) U.S. Cl.
CPC ........ *G06F 19/3456* (2013.01); *A61B 5/0205* (2013.01); *G06F 1/324* (2013.01); *G06F 1/325* (2013.01); *G16H 10/20* (2018.01); *Y02D 10/126* (2018.01)

(58) Field of Classification Search
None
See application file for complete search history.

*Primary Examiner* — Eric S Dejong
(74) *Attorney, Agent, or Firm* — LeClairRyan PLLC

(57) ABSTRACT

The present disclosure relates to a monitoring device and a method of monitoring drug adherence in a clinical trial. In one embodiment, the monitoring device determines that an authenticated user has consumed the medication comprising the drug and further determines that the authenticated user who has consumed the drug is associated with the corresponding monitoring device. Furthermore, the monitoring device determines that the drug has successfully passed through gastrointestinal (GI) tract of the authenticated user based on analysis of biometric signatures of the GI tract. Based on the determination of valid proximity and successful passing of the medication within the GI tract of the authenticated user, the monitoring device reports that the drug adherence by the user is successful. Thus, the disclosed method and the monitoring device determine that only authenticated user has consumed the medication and not just if the medication has been taken by any person.

15 Claims, 4 Drawing Sheets

MONITORING DEVICE AND A METHOD OF MONITORING DRUG ADHERENCE IN A CLINICAL TRIAL

This application claims the benefit of Indian Patent Application Serial No. 6118/CHE/2015 filed Nov. 13, 2015, which is hereby incorporated by reference in its entirety.

FIELD

The present subject matter is related, in general to monitoring system, and more particularly, but not exclusively to a monitoring device and a method of monitoring drug adherence in a clinical trial.

BACKGROUND

Healthcare remains one of the ever evolving and ever demanding fields in pursuit of healthiness. There are numerous ailments that seem to affect the human beings. Many of these ailments have been detected a long time ago but they are not yet treatable. On the other hand, many newer ailments seem to surface every other day. In the endeavor to treat such ailments and improve upon the existing ones pharmaceutical companies, researchers and scientists invent, experiment and test various chemicals to come up with new molecules and drugs for treating these ailments. However, the new molecules and drugs are not directly permitted to be consumed by humans for the obvious reason that these drugs need to be validated using a large scale clinical trial.

In a typical clinical trial, a number of volunteers are enrolled and are prescribed with dosages of particular drug, in the form of tablets or capsules, for pre-defined time duration. This is done in order to verify the effectiveness of the drug for the treating a particular condition over a statistically significant population. It also substantiates whether the drug could be safely consumed by human beings or not. In most cases, the volunteers are paid by these pharma companies running the clinical trial for the drug being tested. In this context, it is of important to confirm whether the drug has been actually consumed by the volunteer or not. In some cases, volunteer may not consume the drug for various reasons thereby reducing the effectiveness and authenticity of the clinical study.

Therefore, there is a need for a monitoring device and a method of monitoring drug adherence in a clinical trial and overcoming the disadvantages and limitations of the existing systems.

SUMMARY

One or more shortcomings of the prior art are overcome and additional advantages are provided through the present disclosure. Additional features and advantages are realized through the techniques of the present disclosure. Other embodiments and aspects of the disclosure are described in detail herein and are considered a part of the claimed disclosure.

Accordingly, the present disclosure relates to a method of monitoring drug adherence in a clinical trial. The method comprising the step of receiving one or more first signals indicative of physiological information associated with a user upon consuming a medication comprising the drug. The method further comprising the step of determining authenticity of the user consuming the medication based on comparison of the physiological information associated with the one or more first signals with previously stored physiological information associated with a plurality of concerned users. Upon determining authenticity of the user, valid proximity of the monitoring device to the medication consumed by the authenticated user is determined based on signal strength associated with one or more second signals received from the medication. Upon determining valid proximity, successful passing of the medication within gastrointestinal (GI) tract of the user is determined based on one or more biometric signatures generated by the medication during the passing within the GI tract of the authenticated user. Based on determination of valid proximity of the monitoring device with the medication and successful passing of the medication within the GI tract of the authenticated user, successful drug adherence of the user is reported by the monitoring device.

Further, the present disclosure relates to a system for monitoring drug adherence in a clinical trial. The system comprises at least one first physiological sensor capable of receiving one or more first signals indicative of physiological information associated with a user and a processor coupled with the at least one first physiological sensor. The system further comprises a memory communicatively coupled with the processor, wherein the memory stores processor-executable instructions, which, on execution, cause the processor to receive one or more first signals upon consuming a medication comprising the drug and determine authenticity of the user consuming the medication. The processor is configured to determine the authenticity of the user based on comparison of the physiological information, associated with the one or more first signals, with previously stored physiological information associated with a plurality of concerned users. Upon determining authenticity of the user, the processor is configured to detect valid proximity of the monitoring device to the medication consumed by the authenticated user based on signal strength associated with one or more second signals received from the medication. The processor is further configured to determine successful passing of the medication within gastrointestinal (GI) tract of the user based on one or more biometric signatures generated by the medication during the passing within the GI tract of the authenticated user. Based on determination of valid proximity of the monitoring device with the medication and successful passing of the medication within the GI tract of the authenticated user, the processor is configured to report successful drug adherence of the user.

Furthermore, the present disclosure relates to a non-transitory computer readable medium including instructions stored thereon that when processed by at least one processor cause a system to perform the act of receiving one or more first signals indicative of physiological information associated with the user upon consuming a medication comprising the drug. Further, the instructions cause the processor to determine authenticity of the user consuming the medication based on comparison of the physiological information, associated with the one or more first signals, with previously stored physiological information associated with a plurality of concerned users. The processor is further configured to detect valid proximity of the monitoring device to the medication consumed by the authenticated user based on signal strength associated with one or more second signals received from the medication. Furthermore, the instructions cause the processor to determine successful passing of the medication within gastrointestinal (GI) tract of the user based on one or more biometric signatures generated by the medication during the passing within the GI tract of the authenticated user. The processor is configured to report successful drug adherence of the user based on determination of valid proximity of the monitoring device with the medication and successful passing of the medication within the GI tract of the authenticated user.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The accompanying drawings, which are incorporated in and constitute a part of this disclosure, illustrate exemplary embodiments and, together with the description, serve to explain the disclosed embodiments. In the figures, the leftmost digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which.

Figure 1:
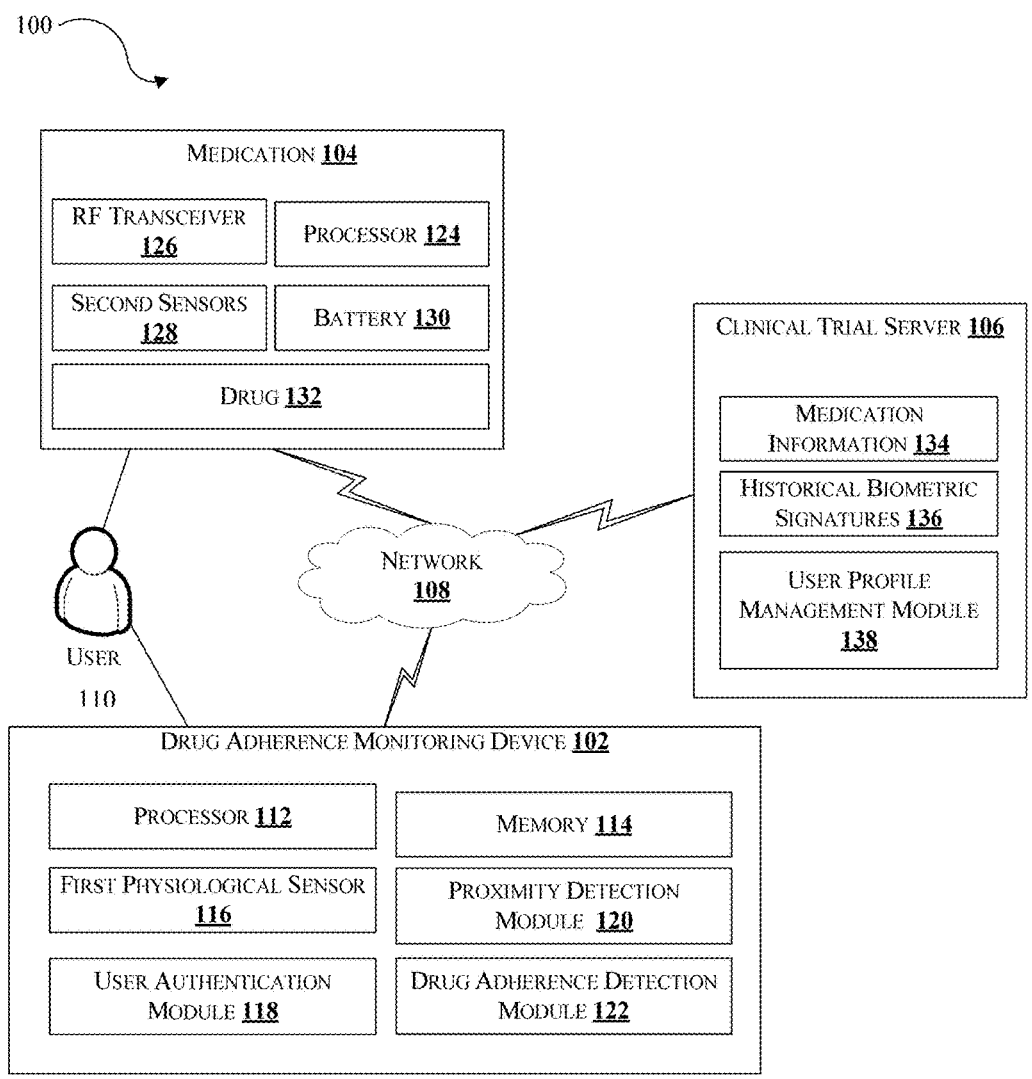
FIG. 1 illustrates an architecture diagram of an exemplary system for monitoring drug adherence in a clinical trial in accordance with some embodiments of the present disclosure.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the spirit and the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or apparatus.

The present disclosure relates to a drug adherence monitoring device and a method of monitoring drug adherence in a clinical trial. In one embodiment, the monitoring device determines that only an authenticated user has consumed the medication comprising the drug. Further, the monitoring device determines that the authenticated user who has consumed the drug is associated with the corresponding monitoring device and furthermore determines that the drug has successfully passed through gastrointestinal (GI) tract of the authenticated user based on analysis of one or more biometric signatures of the GI tract. Based on the determination of valid proximity and successful passing of the medication within the GI tract of the authenticated user, the monitoring device reports that the drug adherence by the user is successful. Thus, the disclosed method and the monitoring device determine that only authenticated user has consumed the medication and not just if the medication has been taken by any person.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

FIG. 1 illustrates an architecture diagram of an exemplary system for monitoring drug adherence in a clinical trial in accordance with some embodiments of the present disclosure.

As shown in FIG. 1, the exemplary system 100 comprises one or more components configured for monitoring drug adherence in a clinical trial. In one embodiment, the exemplary system 100 comprises a drug adherence monitoring device (hereinafter referred to as monitoring device) 102, medication 104 comprising the drug and a clinical trial server 106 connected via a communication network 108. The monitoring device 102 is configured to determine drug adherence by a user 110 based on information received from the medication 104. In one embodiment, the monitoring device 102 comprises at least a processor 112, a memory 114, at least one first physiological sensor 116, a user authentication module 118, a proximity detection module 120 and a drug adherence detection module 122 to determine the drug adherence by the user 110. The monitoring device 102 communicates with the medication 104 and receives information related to the drug from the medication 104 to determine the drug adherence by the user 110.

In one implementation, the monitoring device 102 communicates with the medication 104 using wireless technology such as Bluetooth for example. In another implementation, the monitoring device 102 communicates with the medication 104 via the communication network 108. The medication 104 may be for example a swallowable/ingestible pill or tablet, capable of being consumed by the user 110 undergoing the clinical trial. The medication 104 comprises one or more components made of bio-friendly material that can be easily adaptable by the body of the user 110. In one embodiment, the medication 104 comprises the one or more components including at least a processor 124 and a RF transceiver 126 coupled with the processor 124. The medication 104 further comprises one or more second sensors 128, a battery 130 and drug 132. The one or more second sensors 128 may be for example, an accelerometer, a pH and a temperature sensor and so on capable of collecting information related to acceleration of the medication 104 within gastrointestinal (GI) tract of the user 110, pH level and temperature of the GI tract of the user 110 when the drug 132 is being absorbed by the GI tract of the user 110.

Upon collecting the related information by the one or more sensors 128, the RF transceiver 126 of the medication 104 transmits the collected information to the monitoring device 102. The battery 130 is capable of providing the necessary power supply to enable the transmission of the collected information to the monitoring device 102. In one example, the battery 130 is configured to last around 6 to 8 hours.

In another example, the battery 130 is configured with an energy harvesting mechanism comprising bimetallic electrodes mounted on the surface of the medication 104 to generate the necessary power supply based on the fluid of the GI tract of the user 110. The monitoring device 102 determines drug adherence based on the received information and transmits the drug adherence results to the clinical trial server 106.

In one embodiment, the clinical trial server 106 may be configured by an interested company or organization to conduct the clinical trials and evaluate the results to determine the drug effectiveness. The clinical trial server 106 may also be configured to track information 134 related to the medication 104 including medication identification (ID), dosage information of the medication 104 and so on. The clinical trial server 106 is further configured to store historical biometric signatures 136 of one or more users previously recorded during clinical trials conducted in the past. The clinical trial server 106 also comprises a user profile management module 138 configured to update one or more user profiles with corresponding biometric signatures and drug adherence results provided by the monitoring device 102.

Figure 2:
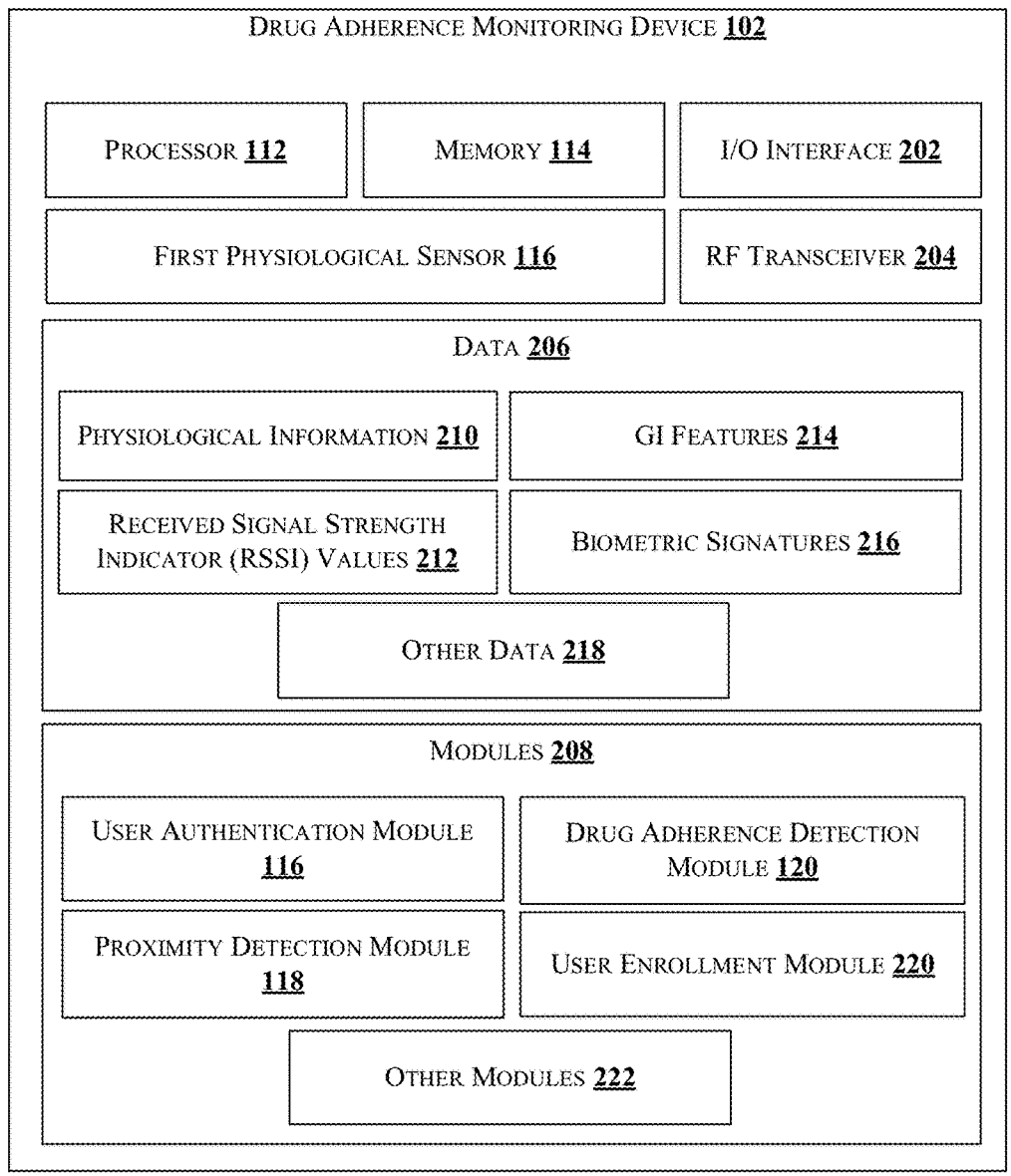
FIG. 2 illustrates an exemplary block diagram of a monitoring device of FIG. 1 in accordance with some embodiments of the present disclosure.

The monitoring device 102 may be a typical monitoring device as illustrated in FIG. 2. In one example, the monitoring device 102 may be one of a wearable device, a hand held device and an embedded device. The monitoring device 102 comprises the processor 112, the memory 114, the first physiological sensor 116, I/O interface 202 and an RF transceiver 204. The I/O interface 202 is coupled with the processor 112 and an I/O device. The I/O device is configured to receive inputs via the I/O interface 202 and transmit outputs for displaying in the I/O device via the I/O interface 202. The first physiological sensor may be for example, an Electrocardiogram (ECG) sensor, capable of obtaining signals indicative of the heart rate. The RF transceiver 204 is capable of receiving and transmitting information in one or more signals representing the said information.

The monitoring device 102 further comprises data 206 and modules 208. In one implementation, the data 206 and the modules 208 may be stored within the memory 114. In one example, the data 206 may include physiological information 210, Received Signal Strength Indicator (RSSI) 212, gastrointestinal (GI) features 214, biometric signatures 216 and other data 218. In one embodiment, the data 206 may be stored in the memory 114 in the form of various data structures. Additionally, the aforementioned data can be organized using data models, such as relational or hierarchical data models. The other data 218 may be also referred to as reference repository for storing recommended implementation approaches as reference data. The other data 218 may also store data, including temporary data and temporary files, generated by the modules 208 for performing the various functions of the monitoring device 102.

The modules 208 may include, for example, the user authentication module 116, the proximity detection module 118, the drug adherence detection module 120 and a user enrollment module 220. The modules 208 may also comprise other modules 222 to perform various miscellaneous functionalities of the monitoring device 102. It will be appreciated that such aforementioned modules may be represented as a single module or a combination of different modules. The modules 208 may be implemented in the form of software, hardware and/or firmware.

In operation, the medication 104 is activated and consumed by the user 110. In one embodiment, the user 110 consuming the medication 104 is a registered user enrolled with the clinical trial server 106 associated with the interested company or organization. In one implementation, the user enrollment module 220 is configured to register one or more concerned users with the clinical trial server 106 by creating one or more corresponding user profiles and storing the one or more user profiles in the clinical trial server 106. For this purpose, the one or more concerned users are made to consume a dummy medication without any drug 130. The first physiological sensor 116, for example, ECG sensor, is configured to obtain one or more test physiological signals indicative of physiological information i.e., ECG signature, associated with the one or more users.

Based on the physiological information, the drug adherence detection module 120 is configured to generate one or more test biometric signatures, for example GI signatures, associated with the GI tract of the one or more concerned users and determine a test probability value indicating possibility of passing or non-passing of the dummy medication within the GI tract of the one or more concerned users. Upon determination, the user enrollment module 220 updates the one or more user profiles stored in the clinical trial server 106 with corresponding historical biometric signatures 136 i.e., ECG signatures and GI signatures. Further, the user enrollment module 220 updates the one or more user profiles with the corresponding test probability value determined corresponding to the one or more concerned users.

During the clinical trial, the medication 104 is activated before consumption by the user 110 and drug adherence is determined by the monitoring device 102 based on the activity of the medication 104. In one embodiment, the medication 104 is automatically activated and powered ON by triggering an in-built activation switch coupled with the battery 130 of the medication 104. In another embodiment, the medication is manually activated by the user 110 by applying a predetermined pressure on the battery 130. Upon activation, the medication 104 is consumed by the user 110 and the monitoring device 102 determines the drug adherence of the user 110 based on the information received from the medication 104 consumed by the user 110.

In one embodiment, the monitoring device 102 is configured to determine authenticity of the user 110 consumed the medication 104. In other words, the monitoring device 102 determines as to whether the user 110 consumed the medication 104 is an authenticated user or not. In one implementation, the user authentication module 118 determines the authenticity of the user 110 associated with the monitoring device 102. The user authentication module 118 receives one or more first signals indicative of physiological information associated with the user 110 via the first physiological sensor 116. In one example, the physiological information may be ECG information obtained via the first physiological sensor, for example an ECG sensor and the ECG information may include time and frequency domain features. The user authentication module 118 receives the physiological information and compares the received physiological information with previously stored physiological information associated with one or more concerned users enrolled with the clinical trial server 106. Based on the comparison, the user authentication module 118 determines that the user 110 who has consumed the medication 104 is a valid user if there is a match in the physiological information. In another implementation, the user authentication module 118 may determine authenticity of the user 110 using any known ECG-based authentication techniques.

If the user authentication module 118 determines that the user 110 is not a valid user, then the monitoring device 102 generates an alarm signal and sends a report to the clinical trial server 106 indicating the unauthenticated consumption of the medication 104. In such cases, the user enrollment module 220 registers the user 110 with the clinical trial server 106 and the user authentication module 118 resumes the authentication. Upon determining the user 110 as valid and authenticated user, the monitoring device 102 determines proximity of the medication 104 to the monitoring device 102 to determine that the medication 104 is being consumed by the same user who has been authenticated by the monitoring device 102.

In one embodiment, the proximity detection module 118 is configured to determine proximity of the medication 104 to the user 110 based on information associated with the one or more second signals transmitted by the medication 104 via the RF transceiver 126. In one implementation, the proximity detection module 118 receives the one or more second signals from the one or more second sensors 128 of the medication 104 via the RF transceiver 204. The proximity detection module 118 determines the strength of the one or more second signals for example, Received Signal Strength Indicator (RSSI) values of the one or more second signals and compares with a predetermined threshold value. Based on the comparison, the proximity detection module 118 determines the acceptable or valid proximity of the medication 104 for example, 30 to 60 cms, ensuring that the medication 104 is consumed by the same user 110 who has been authenticated by the monitoring device 102.

In another embodiment, the proximity detection module 118 determines the proximity of the medication 104 to the monitoring device 102 using Near Field Communication (NFC) tech for example. The proximity detection module 118 receives the one or more second signals from the one or more second sensors 128 of the medication 104 when the medication 104 is tapped onto the monitoring device 102 before consumption of the medication 104. The proximity detection module 118 compares the strength of the one or more second signals with the predetermined threshold value and determines valid proximity of the medication 104 based on the comparison. If the proximity detection module 118 determines unacceptable or invalid proximity of the medication 104 to the monitoring device 102, then the monitoring device 102 generates an alarm signal indicating the invalid proximity and transmits a corresponding report to the clinical trial server 106 for further operations. Upon determining valid proximity of the medication 104, the monitoring device 102 determines the drug adherence of the user 110.

In one embodiment, the drug adherence detection module (hereinafter referred to as DAD module) 120 detect the passage of the medication 104 within the GI tract of the user 110. The DAD module 120 derives one or more physiological information associated with the one or more second signals received from the medication 104 during the passing within the GI tract of the user 110. In one example, the DAD module 120 derives the one or more physiological information including acceleration, pH and temperature information associated with the medication 104 when the medication 104 is passing through the GI tract of the user 110. Based on the derived information, the DAD module 120 determines one or more features associated with the GI tract, for example, a long term feature, a short term feature and peristaltic feature. Long term features, for example, relate to mean and variance of the one or more signals for a time window of 5 to 10 seconds. Short term features are mean and variance of the one or more signals for a time window of for example, 1 to 2 seconds. Peristaltic features is defined as histogram bin count of real and imaginary frequency components of the accelerometer, pH and temperature signatures taken over a time window of for example, 10 to 20 seconds. Based on the one or more features thus determined, the DAD module 120 generates one or more biometric signatures associated with the GI tract and determine probability of passing of the medication 104 within the GI tract based on the one or more biometric signatures thus generated.

In one embodiment, the DAD module 120 compares the one or more biometric signatures thus generated with previously stored historic biometric signatures 136 of the clinical trial server 106. Based on the comparison, the DAD module 120 determines the probability value corresponding to the one or more matching biometric signatures and compares the probability value with a predetermined threshold probability value, for example 0.6. In one implementation, the predetermined threshold probability value is determined through empirical methods. If the DAD module 120 determines that the probability value exceeds the predetermined threshold probability value, then the DAD module 120 determines that the medication 104 has passed through the GI tract of the user 110. Otherwise, the DAD module 120 generates an alarm signal indicating the non-passing of the medication 104 within the GI tract of the user 110 and transmits a corresponding report to the clinical trial server 106 for further operations.

Based on successful authentication of the user 110, valid proximity of the medication 104 to the monitoring device 102 and successful passing of the medication 104 within the GI tract of the user 110, the DAD module 120 generates a report indicating successful drug adherence by the user 110 and transmits the report to the clinical trial server 106. In one example, the generated report comprises information associated with the medication 104, one or more biometric signatures determined by the DAD module, test probability value and success/failure status of the drug adherence. On receiving the report, the user profile management module 138 of the clinical trial server 106 updates the user profile of the user 110 with corresponding probability value and derived features for future use. Thus, the system 100 enables monitoring of drug adherence by user identifying any deviation instances where users have not taken the drug and where unauthenticated users have taken the drug and still further whether the drug has successfully passed within the body of the user.

Figure 3:
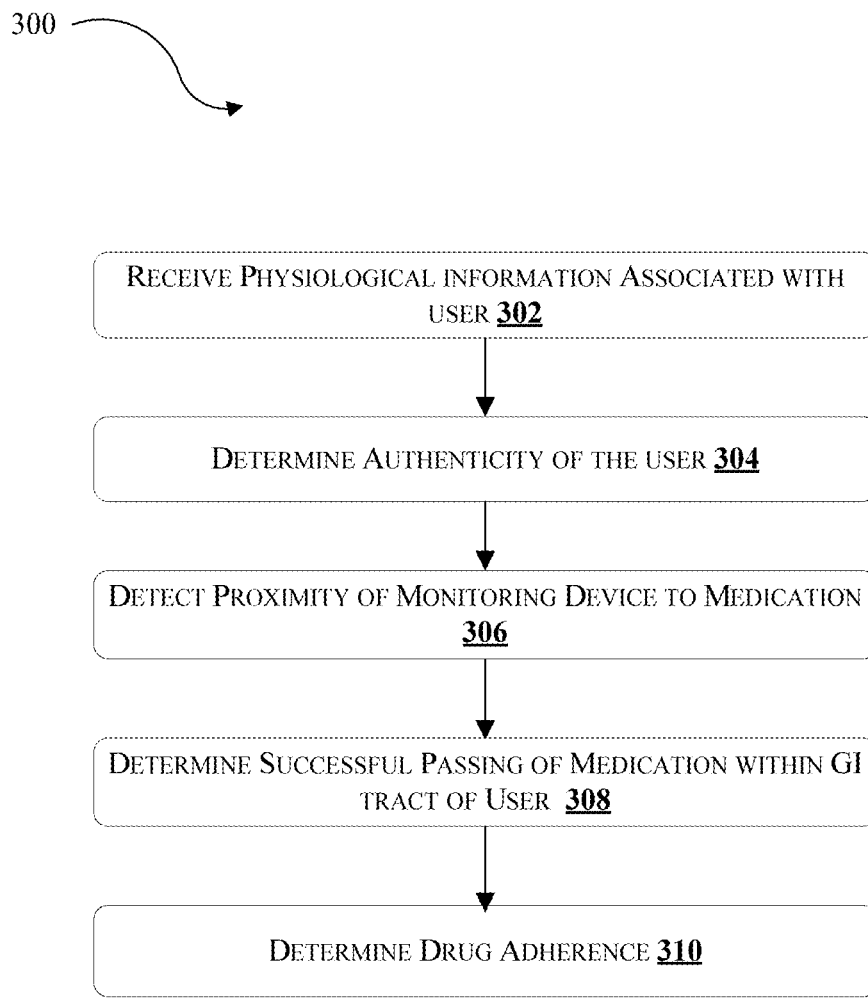
FIG. 3 illustrates a flowchart of an exemplary method of monitoring drug adherence in a clinical trial in accordance with some embodiments of the present disclosure.

FIG. 3 illustrates a flowchart of a method of monitoring drug adherence in a clinical trial in accordance with some embodiments of the present disclosure.

As illustrated in FIG. 3, the method 300 comprises one or more blocks implemented by the processor 112 for monitoring drug adherence in a clinical trial. The method 300 may be described in the general context of computer executable instructions. Generally, computer executable instructions can include routines, programs, objects, components, data structures, procedures, modules, and functions, which perform particular functions or implement particular abstract data types.

The order in which the method 300 is described is not intended to be construed as a limitation, and any number of the described method blocks can be combined in any order to implement the method 300. Additionally, individual blocks may be deleted from the method 300 without departing from the spirit and scope of the subject matter described herein. Furthermore, the method 300 can be implemented in any suitable hardware, software, firmware, or combination thereof.

At block 302, receive physiological information associated with the user. In one embodiment, the user authentication module 118 receives one or more first signals indicative of physiological information associated with the user 110 via the first physiological sensor 116. In one example, the physiological information may be ECG information obtained via the first physiological sensor, for example an ECG sensor.

At block 304, determine authenticity of the user. In one embodiment, the user authentication module 118 determines the authenticity of the user 110 associated with the monitoring device 102. The user authentication module 118 receives the one or more first signals indicative of physiological information associated with the user 110 via the first physiological sensor 116 and compares the received physiological information with previously stored physiological information associated with one or more concerned users enrolled with the clinical trial server 106. Based on the comparison, the user authentication module 118 determines that the user 110 who has consumed the medication 104 is a valid user if there is a match in the physiological information. If the user authentication module 118 determines that the user 110 is not a valid user, then the monitoring device 102 generates an alarm signal and sends a report to the clinical trial server 106 indicating the unauthenticated consumption of the medication 104. Upon determining the user 110 as valid and authenticated user, the monitoring device 102 determines proximity of the medication 104 to the monitoring device 102 to determine that the medication 104 is being consumed by the same user who has been authenticated by the monitoring device 102.

At block 306, detect proximity of the monitoring device to the medication. In one embodiment, the proximity detection module 118 is configured to determine proximity of the medication 104 to the user 110 based on information associated with the one or more second signals transmitted by the medication 104 via the RF transceiver 126. In one implementation, the proximity detection module 118 receives the one or more second signals from the one or more second sensors 128 of the medication 104 via the RF transceiver 204. The proximity detection module 118 determines the strength of the one or more second signals for example, Received Signal Strength Indicator (RSSI) values of the one or more second signals and compares with a predetermined threshold value. Based on the comparison, the proximity detection module 118 determines the acceptable or valid proximity of the medication 104 ensuring that the medication 104 is consumed by the same user 110 who has been authenticated by the monitoring device 102.

In another embodiment, the proximity detection module 118 determines the proximity of the medication 104 to the monitoring device 102 using Near Field Communication (NFC) tech for example. The proximity detection module 118 receives the one or more second signals from the one or more second sensors 128 of the medication 104 when the medication 104 is tapped onto the monitoring device 102 before consumption of the medication 104. The proximity detection module 118 compares the strength of the one or more second signals with the predetermined threshold value and determines valid proximity of the medication 104 based on the comparison. If the proximity detection module 118 determines unacceptable or invalid proximity of the medication 104 to the monitoring device 102, then the monitoring device 102 generates an alarm signal indicating the invalid proximity and transmits a corresponding report to the clinical trial server 106 for further operations. Upon determining valid proximity of the medication 104, the monitoring device 102 determines the drug adherence of the user 110.

At block 308, determine successful passing of the medication within the GI tract of the user. In one embodiment, the DAD module 120 detects the passage of the medication 104 within the GI tract of the user 110. The DAD module 120 derives one or more physiological information associated with the one or more second signals received from the medication 104 during the passing within the GI tract of the user 110. In one example, the DAD module 120 derives the one or more physiological information including acceleration, pH and temperature information associated with the medication 104 when the medication 104 is passing through the GI tract of the user 110. Based on the derived information, the DAD module 120 determines one or more features associated with the GI tract, for example, a long term feature, a short term feature and peristaltic feature. Based on the one or more features thus determined, the DAD module 120 generates one or more biometric signatures associated with the GI tract and determine probability of passing of the medication 104 within the GI tract based on the one or more biometric signatures thus generated.

In one embodiment, the DAD module 120 compares the one or more biometric signatures thus generated with previously stored historic biometric signatures 136 of the clinical trial server 106. Based on the comparison, the DAD module 120 determines the probability value corresponding to the one or more matching biometric signatures and compares the probability value with a predetermined threshold probability value. If the DAD module 120 determines that the probability value exceeds the predetermined threshold probability value, then the DAD module 120 determines that the medication 104 has passed through the GI tract of the user 110. Otherwise, the DAD module 120 generates an alarm signal indicating the non-passing of the medication 104 within the GI tract of the user 110 and transmits a corresponding report to the clinical trial server 106 for further operations.

At block 310, determine drug adherence. In one embodiment, the monitoring device determines successful drug adherence by the user based on successful authentication of the user 110, valid proximity of the medication 104 to the monitoring device 102 and successful passing of the medication 104 within the GI tract of the user 110. In one implementation, the DAD module 120 generates a report indicating successful drug adherence by the user 110 and transmits the report to the clinical trial server 106. On receiving the report, the user profile management module 138 of the clinical trial server 106 updates the user profile of the user 110 with corresponding probability value and derived features for future use.

Thus, the system 100 enables monitoring of drug adherence by user identifying any deviation instances where users have not taken the drug and where unauthenticated users have taken the drug and still further whether the drug has successfully passed within the body of the user.

Figure 4:
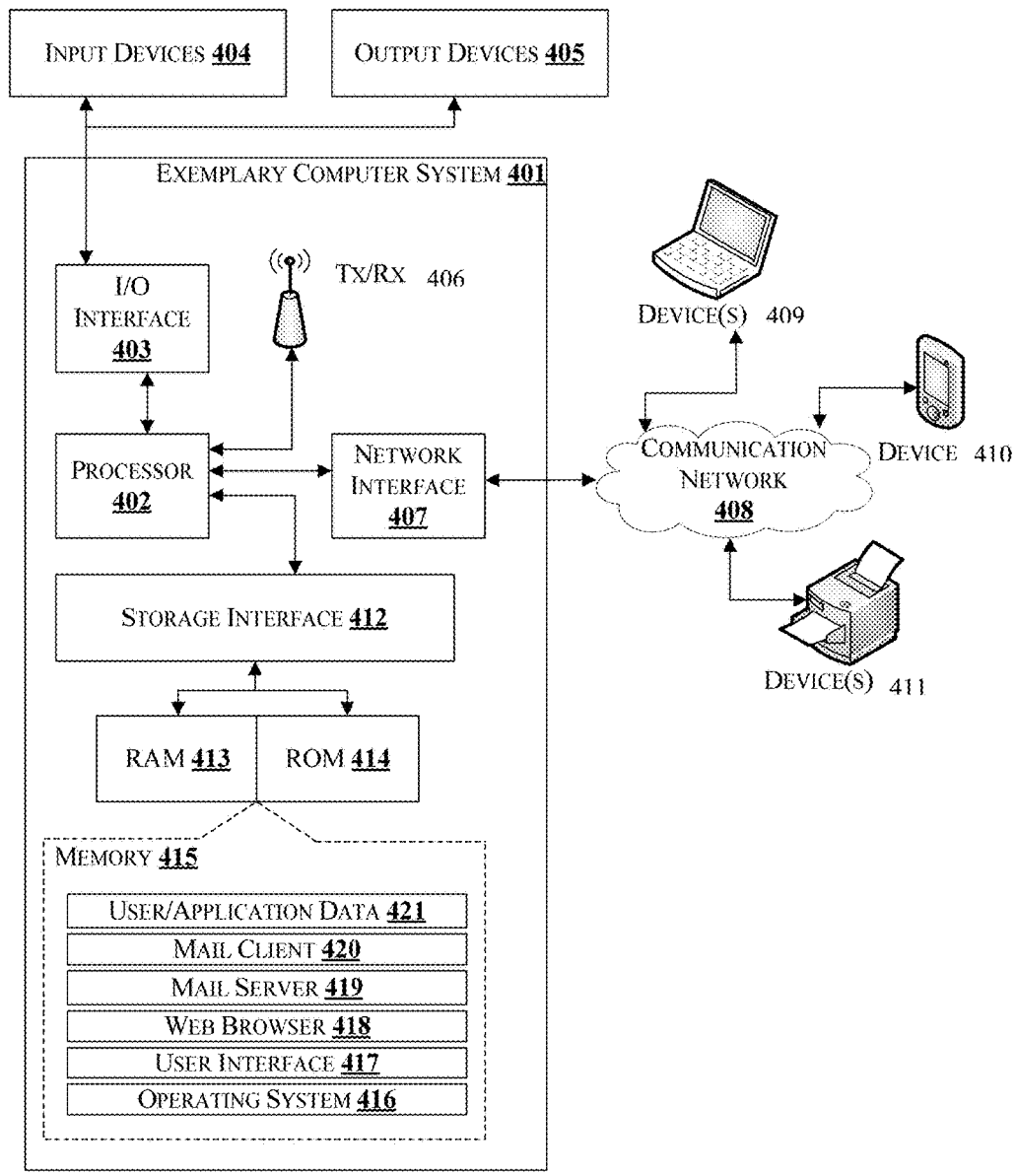
FIG. 4 is a block diagram of an exemplary computer system for implementing embodiments consistent with the present disclosure.

FIG. 4 is a block diagram of an exemplary computer system for implementing embodiments consistent with the present disclosure.

Variations of computer system 401 may be used for implementing all the computing systems that may be utilized to implement the features of the present disclosure. Computer system 401 may comprise a central processing unit ("CPU" or "processor") 402. Processor 402 may comprise at least one data processor for executing program components for executing user- or system-generated requests. The processor may include specialized processing units such as integrated system (bus) controllers, memory management control units, floating point units, graphics processing units, digital signal processing units, etc. The processor 402 may include a microprocessor, such as AMD Athlon, Duron or Opteron, ARM's application, embedded or secure processors, IBM PowerPC, Intel's Core, Itanium, Xeon, Celeron or other line of processors, etc. The processor 402 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

Processor 402 may be disposed in communication with one or more input/output (I/O) devices via I/O interface 403. The I/O interface 403 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 403, the computer system 401 may communicate with one or more I/O devices. For example, the input device 404 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc. Output device 405 may be a printer, fax machine, video display (e.g., cathode ray tube (CRT), liquid crystal display (LCD), light-emitting diode (LED), plasma, or the like), audio speaker, etc. In some embodiments, a transceiver 406 may be disposed in connection with the processor 402. The transceiver may facilitate various types of wireless transmission or reception. For example, the transceiver may include an antenna operatively connected to a transceiver chip (e.g., Texas Instruments WiLink WL1283, Broadcom BCM4750IUB8, Infineon Technologies X-Gold 618-PMB9800, or the like), providing IEEE 802.11a/b/g/n, Bluetooth, FM, global positioning system (GPS), 2G/3G HSDPA/HSUPA communications, etc.

In some embodiments, the processor 402 may be disposed in communication with a communication network 408 via a network interface 407. The network interface 407 may communicate with the communication network 408. The network interface 407 may employ connection protocols including, without limitation, direct connect, Ethernet (e.g., twisted pair 10/40/400 Base T), transmission control protocol/internet protocol (TCP/IP), token ring, IEEE 802.11a/b/g/n/x, etc. The communication network 408 may include, without limitation, a direct interconnection, local area network (LAN), wide area network (WAN), wireless network (e.g., using Wireless Application Protocol), the Internet, etc. Using the network interface 407 and the communication network 408, the computer system 401 may communicate with devices 409, 410, and 411. These devices may include, without limitation, personal computer(s), server(s), fax machines, printers, scanners, various mobile devices such as cellular telephones, smartphones (e.g., Apple iPhone, Blackberry, Android-based phones, etc.), tablet computers, eBook readers (Amazon Kindle, Nook, etc.), laptop computers, notebooks, gaming consoles (Microsoft Xbox, Nintendo DS, Sony PlayStation, etc.), or the like. In some embodiments, the computer system 401 may itself embody one or more of these devices.

In some embodiments, the processor 402 may be disposed in communication with one or more memory devices (e.g., RAM 413, ROM 414, etc.) via a storage interface 412. The storage interface may connect to memory devices including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc.

The memory 415 may store a collection of program or database components, including, without limitation, an operating system 416, user interface application 417, web browser 418, mail server 419, mail client 420, user/application data 421 (e.g., any data variables or data records discussed in this disclosure), etc. The operating system 416 may facilitate resource management and operation of the computer system 401. Examples of operating systems include, without limitation, Apple Macintosh OS X, UNIX, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like. User interface 417 may facilitate display, execution, interaction, manipulation, or operation of program components through textual or graphical facilities. For example, user interfaces may provide computer interaction interface elements on a display system operatively connected to the computer system 401, such as cursors, icons, check boxes, menus, scrollers, windows, widgets, etc. Graphical user interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, the computer system 401 may implement a web browser 418 stored program component. The web browser may be a hypertext viewing application, such as Microsoft Internet Explorer, Google Chrome, Mozilla Firefox, Apple Safari, etc. Secure web browsing may be provided using HTTPS (secure hypertext transport protocol), secure sockets layer (SSL), Transport Layer Security (TLS), etc. Web browsers may utilize facilities such as AJAX, DHTML, Adobe Flash, JavaScript, Java, application programming interfaces (APIs), etc. In some embodiments, the computer system 401 may implement a mail server 419 stored program component. The mail server may be an Internet mail server such as Microsoft Exchange, or the like. The mail server may utilize facilities such as ASP, ActiveX, ANSI C++/C#, Microsoft. NET, CGI scripts, Java, JavaScript, PERL, PHP, Python, WebObjects, etc. The mail server may utilize communication protocols such as internet message access protocol (IMAP), messaging application programming interface (MAPI), Microsoft Exchange, post office protocol (POP), simple mail transfer protocol (SMTP), or the like. In some embodiments, the computer system 401 may implement a mail client 420 stored program component. The mail client may be a mail viewing application, such as Apple Mail, Microsoft Entourage, Microsoft Outlook, Mozilla Thunderbird, etc.

In some embodiments, computer system 401 may store user/application data 421, such as the data, variables, records, etc. as described in this disclosure. Such databases may be implemented as fault-tolerant, relational, scalable, secure databases such as Oracle or Sybase. Alternatively, such databases may be implemented using standardized data structures, such as an array, hash, linked list, struct, structured text file (e.g., XML), table, or as object-oriented databases (e.g., using ObjectStore, Poet, Zope, etc.). Such databases may be consolidated or distributed, sometimes among the various computer systems discussed above in this disclosure. It is to be understood that the structure and operation of the any computer or database component may be combined, consolidated, or distributed in any working combination.

As described above, the modules 208, amongst other things, include routines, programs, objects, components, and data structures, which perform particular tasks or implement particular abstract data types. The modules 208 may also be implemented as, signal processor(s), state machine(s), logic circuitries, and/or any other device or component that manipulate signals based on operational instructions. Further, the modules 208 can be implemented by one or more hardware components, by computer-readable instructions executed by a processing unit, or by a combination thereof.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., are non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method of improved monitoring of drug adherence using obtained physiological sensor data from a consumed medication, the method comprising:

receiving, by a physiological sensor of a drug adherence monitoring device, one or more first signals indicative of a first set of physiological data associated with a user subsequent to consumption by the user of a medication comprising a drug and determining, by a processor of the drug adherence monitoring device, authenticity of the user based on a comparison of the first set of physiological data with previously stored physiological data associated with a plurality of users;

receiving, by a first radio frequency (RF) transceiver of the drug adherence monitoring device, one or more second signals from a second RF transceiver of the medication, the second signals indicative of a second set of physiological data, and determining, by the processor of the drug adherence monitoring device, when a proximity to the consumed medication is valid based on a determined signal strength associated with the second signals;

generating, by the processor of the drug adherence monitoring device, one or more biometric signatures based on the second set of physiological data and determining, by the processor of the drug adherence monitoring device, when a passing of the medication within a gastrointestinal (GI) tract of the user is successful based on the biometric signatures, when the determining indicates that the proximity to the consumed medication is valid; and transmitting, by an input/output (I/O) interface of the drug adherence monitoring device, a report indicating successful drug adherence to a clinical trial server via one or more communication networks, when the determining indicates that the passing of the consumed medication within the GI tract of the user is successful.

2. The method as claimed in claim 1, wherein the determining a proximity to the medication further comprises:

comparing a Received Signal Strength Indicator (RSSI) value of each of the second signals with a predetermined threshold value; and determining when a proximity to the medication is valid based on the comparison.

3. The method as claimed in claim 1, wherein the determining when passing of the medication within the GI tract of the user is successful further comprises:

deriving at least acceleration, pH, or temperature data of the medication from the second signals during the passing of the medication within the GI tract of the user;

determining one or more features including at least a long term feature, a short term feature, or a peristaltic feature associated with the GI tract, based on the derived data;

generating the biometric signatures associated with the GI tract based on the determined features;

determining a probability of passing of the medication within the GI tract of the user based on the biometric signatures;

comparing the probability of passing of the medication within the GI tract of the user with a predetermined threshold probability; and determining when passing of the medication within the GI tract of the user is successful based on the comparing.

4. The method as claimed in claim 1, further comprising activating, by the drug adherence monitoring device, the medication by triggering an activation switch coupled with the medication before consumption of the medication by the user.

5. The method as claimed in claim 1, further comprising:

creating, by the drug adherence monitoring device, one or more user profiles for the other users;

obtaining, by the drug adherence monitoring device, one or more test physiological signals indicative of a third set of physiological data associated with the other users upon consumption of a dummy medication;

generating, by the drug adherence monitoring device, one or more test biometric signatures associated with another GI tract of each of the one or more other users;

determining, by the drug adherence monitoring device, a test probability value indicating one of passing or non-passing of the dummy medication within the another GI tract of each of the other users; and updating, by the drug adherence monitoring device, the user profiles with the third set of physiological data and test probability value corresponding to the other users.

6. A drug adherence monitoring device comprising one or more processors and a memory coupled to the one or more processors, the memory comprising programmed instructions stored thereon that, when executed by the one or more processors, cause the one or more processors to:

receive, by a physiological sensor, one or more first signals indicative of a first set of physiological data associated with a user subsequent to consumption by the user of a medication comprising a drug and determine authenticity of the user based on a comparison of the first set of physiological data with previously stored physiological data associated with a plurality of users;

receive, by a first radio frequency (RF) transceiver, one or more second signals from a second RF transceiver of the medication, the second signals indicative of a second set of physiological data, and determine when a proximity to the consumed medication is valid based on a determined signal strength associated with the second signals;

generate one or more biometric signatures based on the second set of physiological data and determine when a passing of the medication within a gastrointestinal (GI) tract of the user is successful based on the biometric signatures, when the determining indicates that the proximity to the consumed medication is valid; and transmit, by an input/output (I/O) interface, a report indicating successful drug adherence to a clinical trial server via one or more communication networks, when the determining indicates that the passing of the consumed medication within the GI tract of the user is successful.

7. The drug adherence monitoring device as claimed in claim 6, wherein the programmed instructions, when executed by the one or more processors, further cause the one or more processors to:

compare a Received Signal Strength Indicator (RSSI) value of each of the second signals with a predetermined threshold value; and determine when a proximity to the medication is valid based on the comparison.

8. The drug adherence monitoring device as claimed in claim 6, wherein the programmed instructions, when executed by the one or more processors, further cause the one or more processors to:

derive at least acceleration, pH, or temperature data of the medication from the second signals during the passing of the medication within the GI tract of the user;

determine one or more features including at least a long term feature, a short term feature, or a peristaltic feature associated with the GI tract, based on the derived data;

generate the biometric signatures associated with the GI tract based on the determined features;

determine a probability of passing of the medication within the GI tract of the user based on the biometric signatures;

compare the probability of passing of the medication within the GI tract of the user with a predetermined threshold probability; and determine when passing of the medication within the GI tract of the user is successful based on the comparing.

9. The drug adherence monitoring device as claimed in claim 6, wherein the programmed instructions, when executed by the one or more processors, further cause the one or more processors to activate the medication by triggering an activation switch coupled with the medication before consumption of the medication by the user.

10. The drug adherence monitoring device as claimed in claim 6, wherein the programmed instructions, when executed by the one or more processors, further cause the one or more processors to:

create one or more user profiles for the other users;

obtain one or more test physiological signals indicative of a third set of physiological data associated with the other users upon consumption of a dummy medication;

generate one or more test biometric signatures associated with another GI tract of each of the other users;

determine a test probability value indicating one of passing or non-passing of the dummy medication within the another GI tract of each of the other users; and update the user profiles with the third set of physiological data and test probability value corresponding to the other users.

11. A non-transitory computer readable medium comprising programmed instructions stored thereon for improved monitoring of drug adherence using obtained physiological sensor data from a consumed medication, which when executed by one or more processors, cause the one or more processors to:

receive, by a physiological sensor, one or more first signals indicative of a first set of physiological data associated with a user subsequent to consumption by the user of a medication comprising a drug and determine authenticity of the user based on a comparison of the first set of physiological data with previously stored physiological data associated with a plurality of users;

receive, by a first radio frequency (RF) transceiver, one or more second signals from a second RF transceiver of the medication, the second signals indicative of a second set of physiological data, and determine when a proximity to the consumed medication is valid based on a determined signal strength associated with the second signals;

generate one or more biometric signatures based on the second set of physiological data and determine when a passing of the medication within a gastrointestinal (GI) tract of the user is successful based on the biometric signatures, when the determining indicates that the proximity to the consumed medication is valid; and transmit, by an input/output (I/O) interface, a report indicating successful drug adherence to a clinical trial server via one or more communication networks, when the determining indicates that the passing of the consumed medication within the GI tract of the user is successful.

12. The non-transitory computer readable medium as claimed in claim 11, wherein the programmed instructions, when executed by the one or more processors, further cause the one or more processors to:
compare a Received Signal Strength Indicator (RSSI) value of each of the second signals with a predetermined threshold value; and
determine when a proximity to the medication is valid based on the comparison.

13. The non-transitory computer readable medium as claimed in claim 11, wherein the programmed instructions, when executed by the one or more processors, further cause the one or more processors to:
derive at least acceleration, pH, or temperature data of the medication from the second signals during the passing of the medication within the GI tract of the user;
determine one or more features including at least a long term feature, a short term feature, or a peristaltic feature associated with the GI tract, based on the derived data;
generate the biometric signatures associated with the GI tract based on the determined features;
determine a probability of passing of the medication within the GI tract of the user based on the biometric signatures;
compare the probability of passing of the medication within the GI tract of the user with a predetermined threshold probability; and
determine when passing of the medication within the GI tract of the user is successful based on the comparing.

14. The non-transitory computer readable medium as claimed in claim 11, wherein the programmed instructions, when executed by the one or more processors, further cause the one or more processors to activate the medication by triggering an activation switch coupled with the medication before consumption of the medication by the user.

15. The non-transitory computer readable medium as claimed in claim 11, wherein the programmed instructions, when executed by the one or more processors, further cause the one or more processors to:
create one or more user profiles for the other users;
obtain one or more test physiological signals indicative of a third set of physiological data associated with the other users upon consumption of a dummy medication;
generate one or more test biometric signatures associated with another GI tract of each of the other users;
determine a test probability value indicating one of passing or non-passing of the dummy medication within the another GI tract of each of the other users; and
update the user profiles with the third set of physiological data and test probability value corresponding to the other users.

* * * * *